US008295576B2

(12) United States Patent
Gadodia et al.

(10) Patent No.: US 8,295,576 B2
(45) Date of Patent: Oct. 23, 2012

(54) SYSTEM AND METHOD FOR AUTOMATED MEDICAL DIAGNOSTIC INTERPRETATION AND REPORT GENERATION

(75) Inventors: Gopal Gadodia, Indian Harbour Beach, FL (US); Shashin Desai, Indian Harbour Beach, FL (US); Anil Patel, Indialantic, FL (US)

(73) Assignee: MedNova, Indialantic, FL (US)

( * ) Notice: Subject to any disclaimer, the term of this patent is extended or adjusted under 35 U.S.C. 154(b) by 817 days.

(21) Appl. No.: 11/990,190

(22) PCT Filed: Aug. 9, 2006

(86) PCT No.: PCT/US2006/031036
§ 371 (c)(1),
(2), (4) Date: Sep. 11, 2008

(87) PCT Pub. No.: WO2007/021745
PCT Pub. Date: Feb. 22, 2007

(65) Prior Publication Data
US 2009/0171225 A1 Jul. 2, 2009

Related U.S. Application Data

(60) Provisional application No. 60/706,453, filed on Aug. 9, 2005.

(51) Int. Cl.
*G06K 9/00* (2006.01)
(52) U.S. Cl. ........ 382/132; 600/407; 600/410; 600/437; 382/128; 382/131
(58) Field of Classification Search .......... 600/407–429, 600/437–469, 473–480; 382/128–132; 705/2
See application file for complete search history.

(56) References Cited

U.S. PATENT DOCUMENTS

| | | | |
|---|---|---|---|
| 5,748,907 A | 5/1998 | Crane | |
| 5,772,585 A | 6/1998 | Lavin et al. | |
| 5,823,948 A * | 10/1998 | Ross et al. | 600/300 |
| 6,029,671 A * | 2/2000 | Stevens et al. | 128/898 |
| 6,314,556 B1 | 11/2001 | DeBusk et al. | |
| 6,801,916 B2 * | 10/2004 | Roberge et al. | 1/1 |
| 7,155,447 B2 * | 12/2006 | Roberge et al. | 1/1 |
| 7,209,578 B2 * | 4/2007 | Saito et al. | 382/128 |
| 7,252,638 B2 * | 8/2007 | Kahn et al. | 600/443 |
| 2002/0111932 A1 * | 8/2002 | Roberge et al. | 707/1 |
| 2003/0083903 A1 * | 5/2003 | Myers | 705/2 |
| 2004/0254816 A1 * | 12/2004 | Myers | 705/2 |
| 2006/0116904 A1 * | 6/2006 | Brem | 705/2 |
| 2009/0319291 A1 * | 12/2009 | Noordvyk et al. | 705/2 |

* cited by examiner

*Primary Examiner* — Sanjay Cattungal
(74) *Attorney, Agent, or Firm* — McDermott Will & Emery LLP

(57) ABSTRACT

Automated medical diagnostic interpretation and report generation for a non-invasive medical diagnostic test, such as an echo cardiogram, is provided. Various dimension measurements and physiological measurements from an echo cardiogram machine are transferred automatically to a computer over an echo cardiogram machine interface. The dimensions and physiological measurements are automatically interpreted by an intelligent interpretation engine running on a computer, generating various machine evaluations. The physician can approve the machine evaluations, overrule them, or make appropriate adjustments. Upon completion of the physician's review, the physician approved interpretations become diagnostic conclusions, and the report containing the results of the physician's review is generated by the report generation engine.

21 Claims, 9 Drawing Sheets

SYSTEM AND METHOD FOR AUTOMATED MEDICAL DIAGNOSTIC INTERPRETATION AND REPORT GENERATION

CROSS-REFERENCES AND RELATED APPLICATIONS

This application is the U.S. National Phase under 35 U.S.C. §371 of International Application No. PCT/US2006/031036, filed on Aug. 9, 2006, which in turn claims priority to U.S. Provisional Application No. 60/706,453, filed Aug. 9, 2005, and entitled "GENERATING AND INTERPRETING PHYSICIAN REPORTS", which is herein incorporated by reference in its entirety for all purposes.

BACKGROUND OF THE INVENTION

1. Field of the Invention

The present invention relates to diagnostic interpretation and reporting for a non-invasive medical diagnostic test. Specifically, the present invention relates to automated medical diagnostic interpretation and report generation for a non-invasive medical diagnostic test.

2. Description of the Related Art

The interpretation and reporting of non-invasive medical diagnostic tests, such as an echo cardiogram test, is a labor intensive process as currently practiced in the field of medical diagnostics. A typical procedure for an echo cardiogram may be as follows. A patient is scheduled for an echo cardiogram. The technician fills out the patient demographics on a form. The technician then administers the test and records the procedure and reading. The study is now placed in the physician's inbox to be interpreted. The physician (normally at the end of a busy day) initiates the study. The physician records the findings on the form and fills out the interpretation. In some cases the abnormalities may be duplicated in an abbreviated conclusion section of the study. Once the form is filled out, it is then placed in the inbox of the transcriber. The transcriber (typically the following day) will type up the report and place it in the inbox of the physician. Once again, the physician will get the study from the inbox and reviews it for correctness. Once the study is approved, it is then filed and/or sent to the referring physician. As can be seen from the above descriptions, the process is labor-intensive and slow, requiring processing by several personnel and the physician and taking several days. The process is also susceptible to errors due to the manual entry and processing at several points in the process.

SUMMARY OF THE INVENTION

Accordingly, the present invention addresses the problems described above by providing a system and a method for automated medical diagnostic interpretation and report generation for a non-invasive medical diagnostic test.

One aspect of the present invention is a method for automated medical diagnostic interpretation and report generation for a non-invasive medical diagnostic test including receiving one or more structural dimension measurements and physiological measurements from the non-invasive medical diagnostic test, interpreting the dimension measurements and physiological measurements, generating a diagnostic evaluation to be reviewed by a physician, and generating a diagnostic report upon completion of the physician's review.

According to another aspect of the invention, a method for automated medical diagnostic interpretation and report generation for an echo cardiogram test includes receiving one or more structural dimension measurements and physiological measurements from the echo cardiogram test which include a measurement of the size of the left ventricle, the left atrium, the aortic root, and the right-sided chambers, a measurement of pericardial effusion, and a measurement of Doppler velocities across one or more heart valves, interpreting the dimension measurements and physiological measurements, generating diagnostic evaluations to be reviewed by a physician which include an evaluation of whether the left ventricle is normal in size or dilated, an evaluation of whether the left ventricle is hypertrophied, an evaluation of calcification, an evaluation of the existence of pathological mass or structure in the cardiac chamber cavity, an evaluation of a severity of pericardial effusion, an evaluation of a severity of regurgitation through a heart valve, an evaluation of tricuspid regurgitation, an evaluation of pulmonary hypertension and an evaluation of aortic and mistral valve stenosis, and generating a diagnostic report upon completion of the physician's review.

According to yet another aspect of the invention, a system for automated medical diagnostic interpretation and report generation for a non-invasive medical diagnostic test includes a computer, a medical diagnostic interpretation engine, and a report generation engine, wherein the medical diagnostic interpretation engine running on the computer receives one or more structural dimension measurements and physiological measurements from the non-invasive medical diagnostic test, interprets the dimension measurements and physiological measurements, and generates a diagnostic evaluation to be reviewed by a physician, and, upon completion of the physician's review, the report generation engine generates a diagnostic report.

According to another aspect of the invention, a system for automated medical diagnostic interpretation and report generation for a non-invasive medical diagnostic test includes a computer, a medical diagnostic interpretation engine, and a report generation engine, wherein the medical diagnostic interpretation engine running on the computer receives one or more structural dimension measurements and physiological measurements from the non-invasive medical diagnostic test, interprets the dimension measurements and physiological measurements, and generates a diagnostic evaluation to be reviewed by a physician, and, upon completion of the physician's review, the report generation engine generates a diagnostic report.

According to yet another aspect of the invention, a system for automated medical diagnostic interpretation and report generation for an echo cardiogram test includes a computer, a medical diagnostic interpretation engine, and a report generation engine, wherein the medical diagnostic interpretation engine running on the computer receives one or more structural dimensions and physiological measurements from the echo cardiogram test which comprise a measurement of the size of the left ventricle, the left atrium, the aortic root, and the right-sided chambers, a measurement of pericardial effusion, and a measurement of Doppler velocities across one or more heart valves, where the medical diagnostic interpretation engine interprets the dimensions and physiological measurements, and generates diagnostic evaluations to be reviewed by a physician including an evaluation of whether the left ventricle is normal in size or dilated, an evaluation of whether the left ventricle is hypertrophied, an evaluation of calcification, an evaluation of the existence of pathological mass or structure in the cardiac chamber cavity, an evaluation of a severity of pericardial effusion, an evaluation of a severity of regurgitation through a heart valve, an evaluation of tricuspid regurgitation, an evaluation of pulmonary hypertension, and an evaluation of aortic and mistral valve stenosis, and, upon completion of the physician's review, the report generation engine generates a diagnostic report.

According to yet another aspect of the invention, computer-executable process steps for automated medical diagnostic interpretation and report generation for an echo cardiogram test include a step for receiving one or more structural dimension measurements and physiological measurements from the echo cardiogram test which includes a measurement of the size of the left ventricle, the left atrium, the aortic root, and the right-sided chambers, a measurement of pericardial effusion, and a measurement of Doppler velocities across one or more heart valves, a step for interpreting the dimension measurements and physiological measurements, a step for generating diagnostic evaluations to be reviewed by a physician which include an evaluation of whether the left ventricle is normal in size or dilated, an evaluation of whether the left ventricle is hypertrophied, an evaluation of calcification, an evaluation of the existence of pathological mass or structure in the cardiac chamber cavity, an evaluation of a severity of pericardial effusion, an evaluation of a severity of regurgitation through a heart valve, an evaluation of tricuspid regurgitation, an evaluation of pulmonary hypertension, and an evaluation of aortic and mistral valve stenosis, and a step for generating a diagnostic report upon completion of the physician's review.

Other and further objects and advantages of the present invention will be further understood and appreciated by those skilled in the art by reference to the following specification, claims, and drawings.

BRIEF DESCRIPTION OF THE DRAWINGS

Referring now to the drawings in which like reference numbers represent corresponding parts throughout:

FIG. 5 illustrates a screen for listing unread echo cardiogram studies according to an embodiment of the present invention;

FIG. 8 illustrates a screen for a physician's reading and interpretation of overall systolic function according to an embodiment of the present invention.

DETAILED DESCRIPTION OF THE INVENTION

Figure 1:
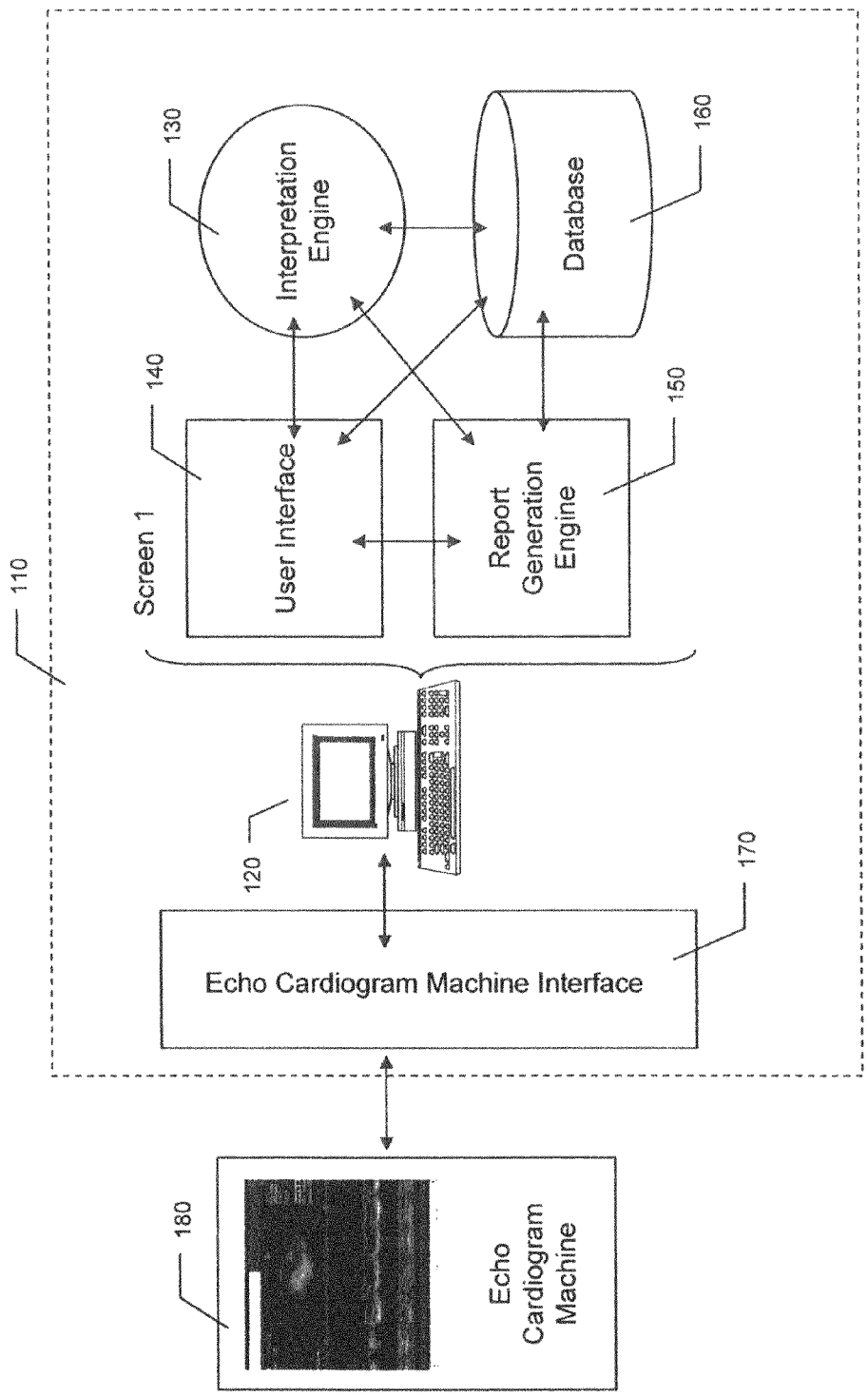
FIG. 1 illustrates a system for automated medical diagnostic interpretation and report generation according to an embodiment of the present invention.

FIG. 1 illustrates a system for automated medical diagnostic interpretation and report generation for a non-invasive medical diagnostic test according to the present invention. As shown in FIG. 1, the system according to the present invention 110 comprises a computer 120, a medical diagnostic interpretation engine 130, user interface 140 running on the computer 120, a report generation engine 150, and a database 160. The system of the present invention may also include an interface 170 for communicating with the non-invasive medical diagnostic test machine 180.

In one embodiment of the present invention, the non-invasive medical diagnostic test is an echo cardiogram. Once a patient is scheduled for an echo cardiogram, the technician enters the patient identification and patient demographics information on the echo cardiogram machine 180. The patient identification and patient demographics information can be automatically transferred to the computer 120 of the present invention over the echo cardiogram machine interface 170. If the patient record already exists in the database 160, the patient information is automatically retrieved from the database 160. On the day of the test, the technician administers the test and inputs the various measurements in the echo cardiogram machine 180. In one embodiment, the echo cardiogram measurements are automatically transferred to the computer 120 over the echo cardiogram machine interface 170. In an alternative embodiment, the echo cardiogram measurements can be entered manually on the computer 120 by the technician without departing from the scope of the present invention.

Similarly, in one embodiment of the present invention, various dimension measurements and physiological measurements are transferred automatically to the computer 120 over the echo cardiogram machine interface 170. In the alternative, the dimension measurements and physiological measurements from the echo cardiogram machine 180 can be entered manually on the computer 120 by the technician without departing from the scope of the present invention.

Upon receiving the dimension measurements and physiological measurements, the interpretation engine 130 interprets the dimensions and physiological measurements based on default values or threshold values which had already been entered into the computer 120 and/or stored in the database 160, and automatically generates diagnostic evaluations. For example, the measurements of the size of the left ventricle, the left atrium, the aortic root, and the right-sided chambers are interpreted by the interpretation engine 130 to create an evaluation of dilation of the left ventricle, the left atrium, the aortic root, and the right-sided chambers. The evaluation can be one of normal in size, mildly dilated, moderately dilated, or severely dilated, without departing from the scope of the present invention. In addition, the thickness of the left ventricle can be interpreted to determine whether the left ventricle is mildly, moderately, or severely hypertrophies—i.e., thicker than normal—without departing from the scope of the present invention.

Figure 2:
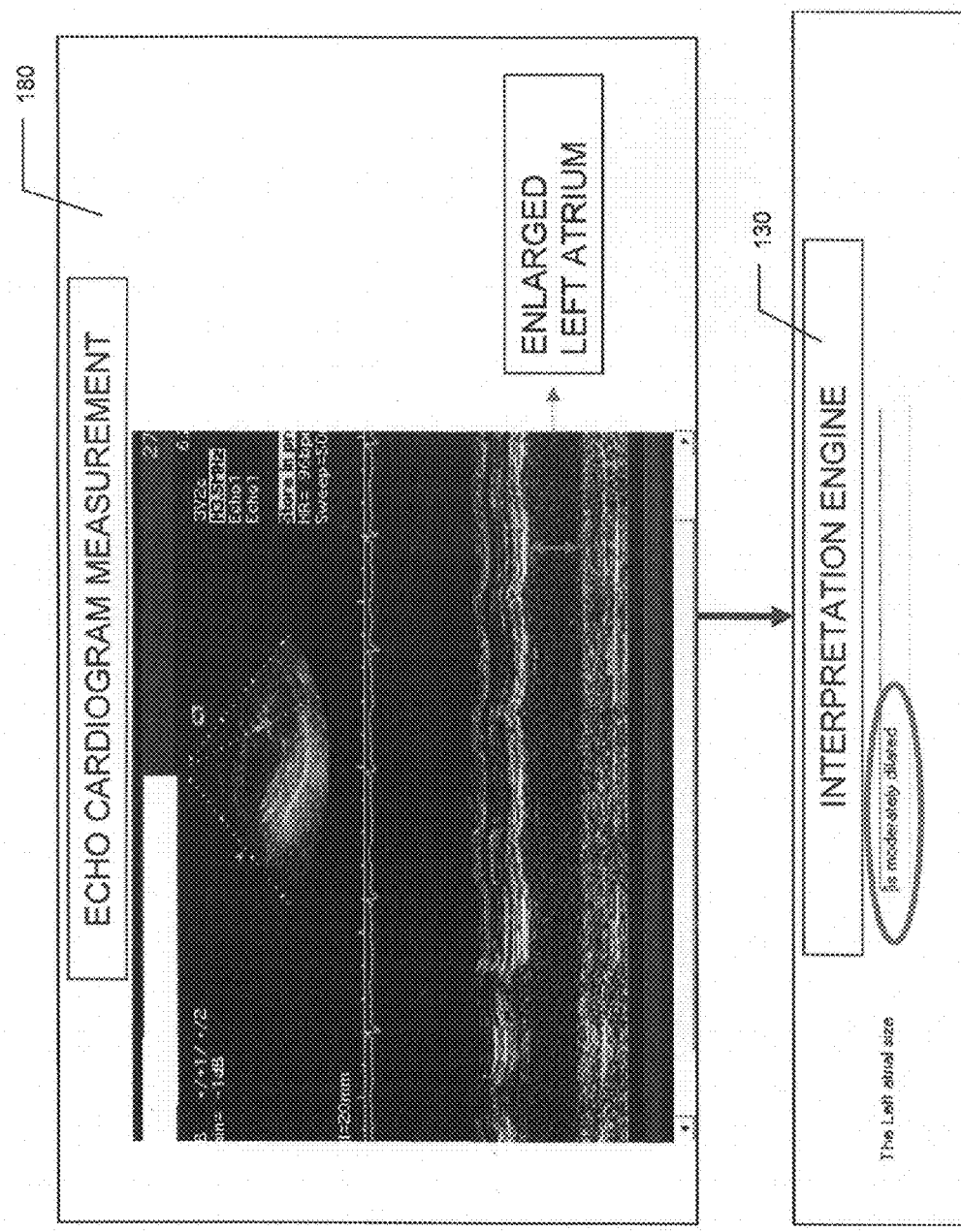
FIG. 2 illustrates an evaluation of left atrium dilation from echo cardiogram measurements by an interpretation engine according to an embodiment of the present invention.

FIG. 2 illustrates an evaluation of left atrium dilation from echo cardiogram measurements by the interpretation engine according to the present invention. As shown in FIG. 2, an echo cardiogram measurement of the size of left atrium is interpreted by the interpretation engine 130 to determine the dilation of the left atrium.

Furthermore, an evaluation of calcification is made utilizing a calcium scoring method used to score calcium that may be present in the valve or the annulus of the aortic and mitral valve. As well-known to those skilled in the art, the scoring method typically depends on the background echogenicity to the echogenicity of the valve. The reflection of the echo (i.e., sound waves traveling and hitting different structures) that returns to the echo cardiogram machine reveals the "echogenicity" of a tissue. A softer tissue has a different reflection back to the machine than a calcified harder structure, and hence tissue differentiation is made based on the strength of the echo reflections. In addition, an evaluation of the existence of pathological mass or structure in the cardiac chamber cavity is made based on the linearity and calcification score. The calcification score of a mass or structure is based on the amount of reflected sonar waves or echo waves deflected back from it.

Also, an evaluation of the severity of pericardial effusion is made automatically by the interpretation engine 130. The pericardial effusion, which is the fluid around the heart cavity, may be measured by autocalipers provided by most of the echo cardiogram machines. The amount of fluid is judged to be mild, moderate or severe, and is measured as 1 mm, 2 mm, 3 mm or more. Hence, the amount of fluid can be measured based on the 2-dimensional measurements of the pericardial fluid by the autocalipers.

The last part of the echo cardiogram study is usually related to the Doppler velocities across the different valves, and most often regurgitant volume is depicted. This Doppler phenomenon is analogous to a Doppler radar view of the weather, wherein the intensity of the Doppler reflection is viewed to judge the presence of heavy precipitation or light precipitation. Similarly, in an echocardiogram, the doctor judges how large a jet is regurgitating back into the cavity. The echocardiogram can also indicate the amount by volume. The amount can also be determined by the width of the jet, which indicates whether the regurgitation is mild, moderate or severe. The regurgitant volume may be related to the velocity of the regurgitation, the volume or area of the chamber occupied by the regurgitant volume, or the diameter of the regurgitation as compared to a normal valve diameter. The ratio of this could delineate whether the regurgitant volume is mild, moderate or severe. All the above modalities can be used to delineate the severity of the regurgitation through a valve.

Figure 3:
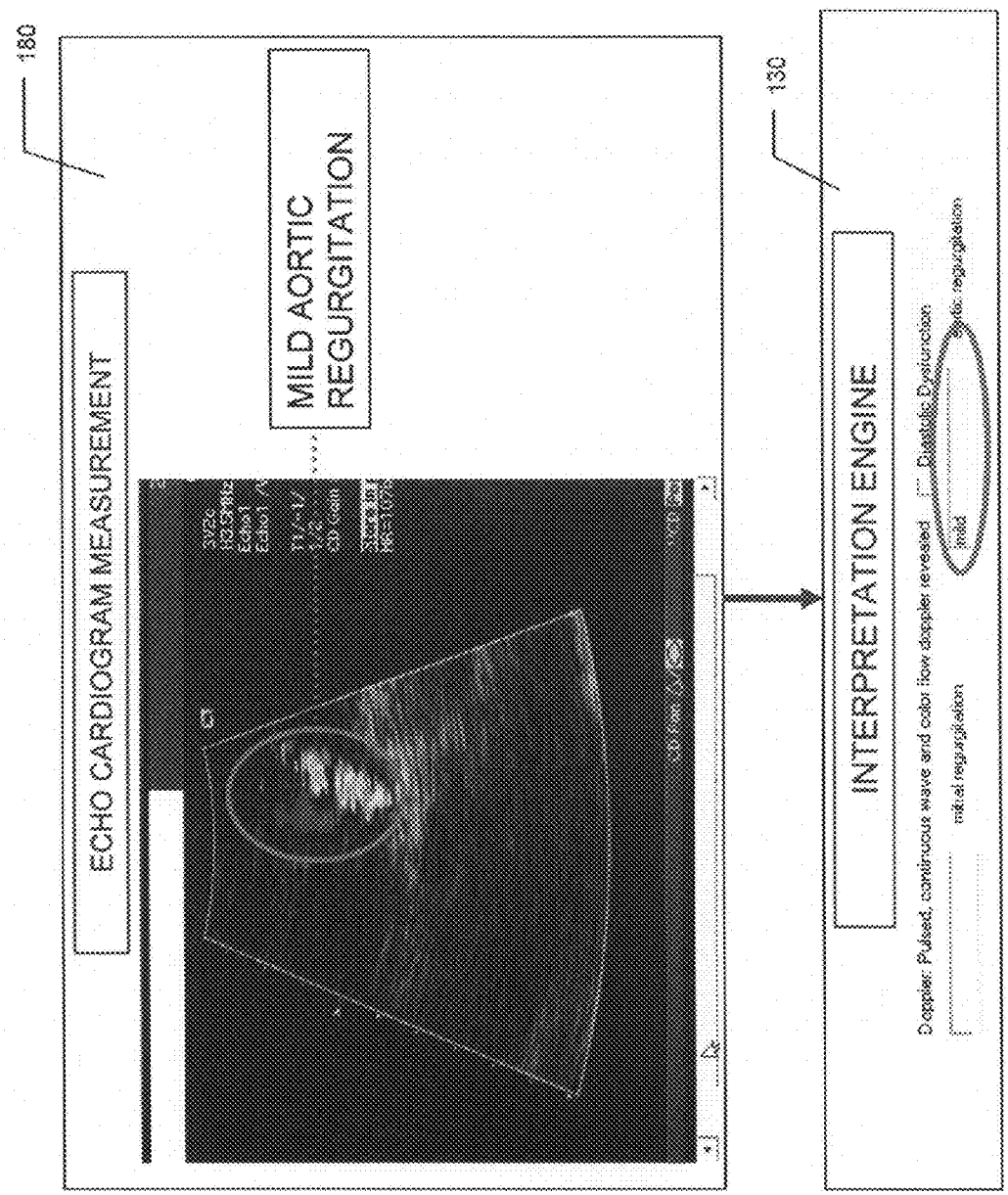
FIG. 3 illustrates an evaluation of aortic regurgitation from echo cardiogram measurements by an interpretation engine according to an embodiment of the present invention.

FIG. 3 illustrates an evaluation of aortic regurgitation from echo cardiogram measurements by the interpretation engine according to the present invention. As shown in FIG. 3, an echo cardiogram measurement of the Doppler velocities is interpreted by the interpretation engine 130 to determine the severity of aortic regurgitation.

In certain embodiments of the present invention, the interpretation engine 130 is implemented utilizing various artificial intelligence technologies such as the neural net and expert system which are well-known in the field of machine learning and artificial intelligence. Any suitable machine intelligence technology can be utilized to embody and encode the expertise and knowledge of domain experts in the intelligent interpretation engine 130 according to the present invention.

Most conventional echocardiogram machines have a calculator and different formulas built into the system for evaluation of tricuspid regurgitation and pulmonary hypertension, and aortic and mitral valve stenosis. In one embodiment, they are directly input from the echo machine 180 to the computer 120.

Figure 4:
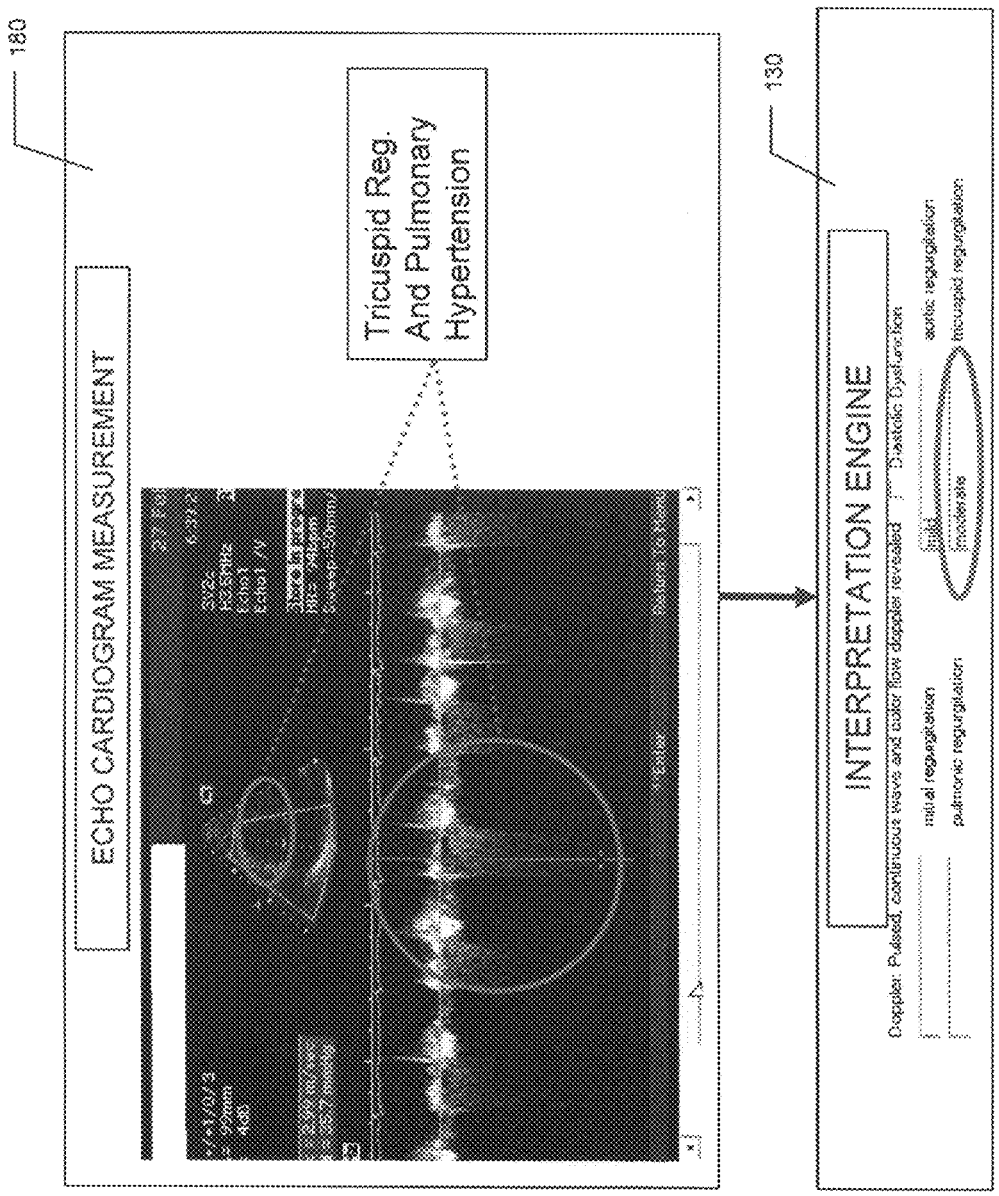
FIG. 4 illustrates an evaluation of tricuspid regurgitation and pulmonary hypertension from echo cardiogram measurements by an interpretation engine according to an embodiment of the present invention.

FIG. 4 illustrates an evaluation of tricuspid regurgitation and pulmonary hypertension from echo cardiogram measurements by the interpretation engine according to the present invention. As shown in FIG. 4, moderate tricuspid regurgitation measurement on the echo cardiogram machine 180 is directly transferred to the interpretation engine 130 running on the computer 120.

When reviewing the echo cardiogram studies, the physician can approve the evaluations made by the interpretation engine 130, make appropriate adjustments, or overrule the machine evaluations. The physician will always be able to overrule and interpret the finding according to the best visualization. Upon completion of the physician's review, the physician approved interpretations become diagnostic conclusions, and the report containing the results of the physician review is generated by the report generation engine 150.

The computer 120 can be any suitable computer known to those skilled in the art, including a PC and a workstation. The computer 120 typically has a CPU, a hard disk, sufficient memory to support graphics computation, a graphics adapter, a display monitor, a keyboard, and a pointing device such as a mouse.

The echo cardiogram machine interface 170 can be implemented as a software or computer program module on the computer 120, or, alternatively, as dedicated hardware module with firmware without departing from the scope of the present invention. The echo cardiogram machine interface 170 can communicate with the echo cardiogram machine 180 over any communication or network link well known to those skilled in the art of computer communication, including, but not limited to, LAN connections such as the Ethernet, Internet connections over various WAN/LAN hardware and TCP/IP protocol with security measures and secure communication protocols if necessary, various serial and/or parallel connections such as an LIS connection over a serial link, and a wireless connection without departing from the scope of the present invention.

The interpretation engine 130, database 160, and report generation engine 150 can be executed from a different computer or server other than the computer 120 without departing from the scope of the present invention.

Organization of displays or screens of the present invention can be implemented utilizing any method or technology well known to those skilled in the art of computer graphics display or graphical user interface (GUI) design, including, but not limited to, various windows-based GUI design such as Microsoft Windows, X-Windows/Motif, and OpenGL, as well as object-oriented GUI design and component-based GUI design, without departing from the scope of the present invention.

Figure 5:
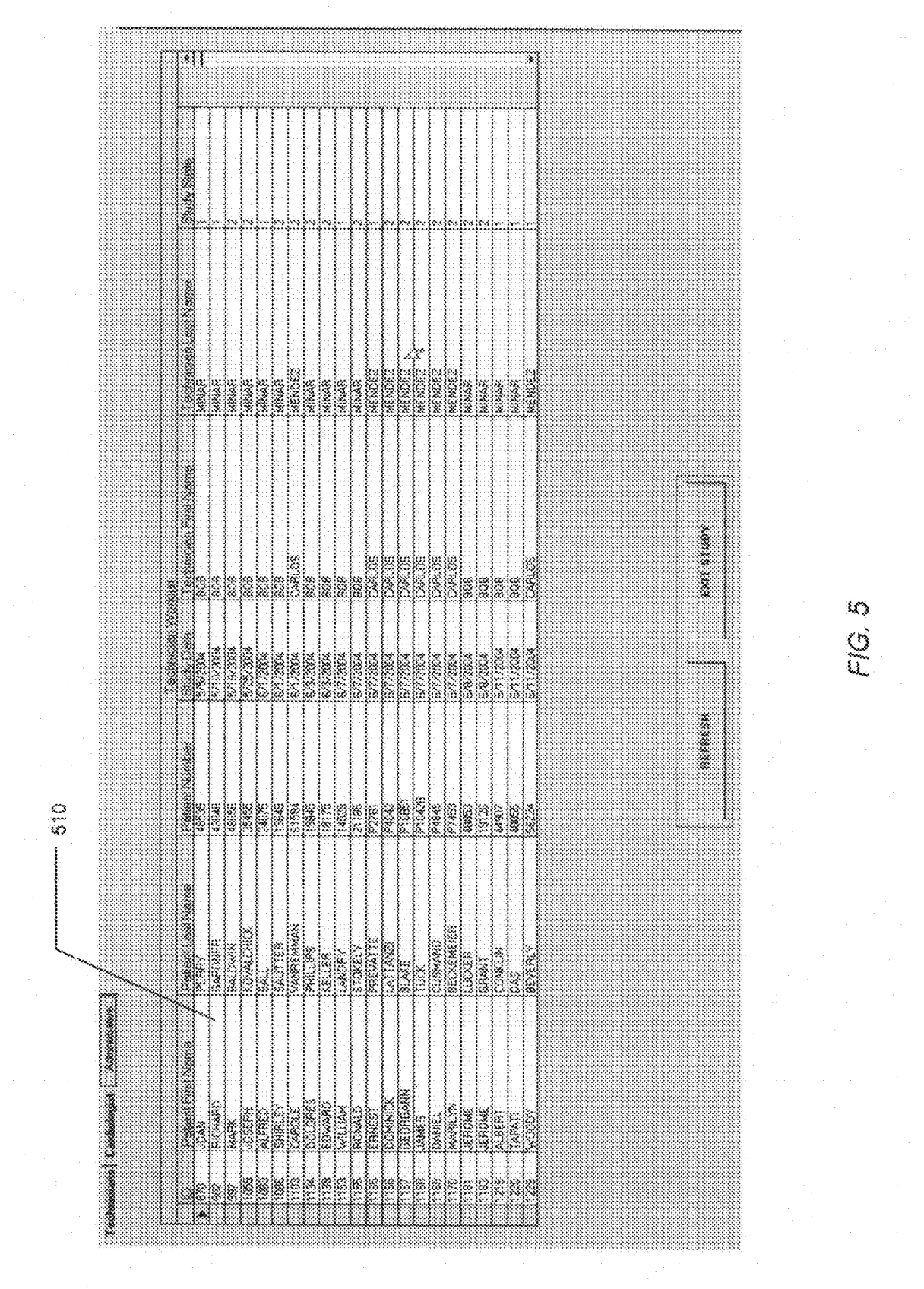

FIG. 5 illustrates a screen for listing unread echo cardiogram studies according to an embodiment of the present invention. As shown in FIG. 5, the administered echo cardiogram tests that have been transferred to the computer 120 are listed on the list area 510. Typically, the list is retrieved from the patient and test records stored in the database 160. To initiate a review of an unread study, the physician clicks on the desired patient entry on the list 510.

Figure 6:
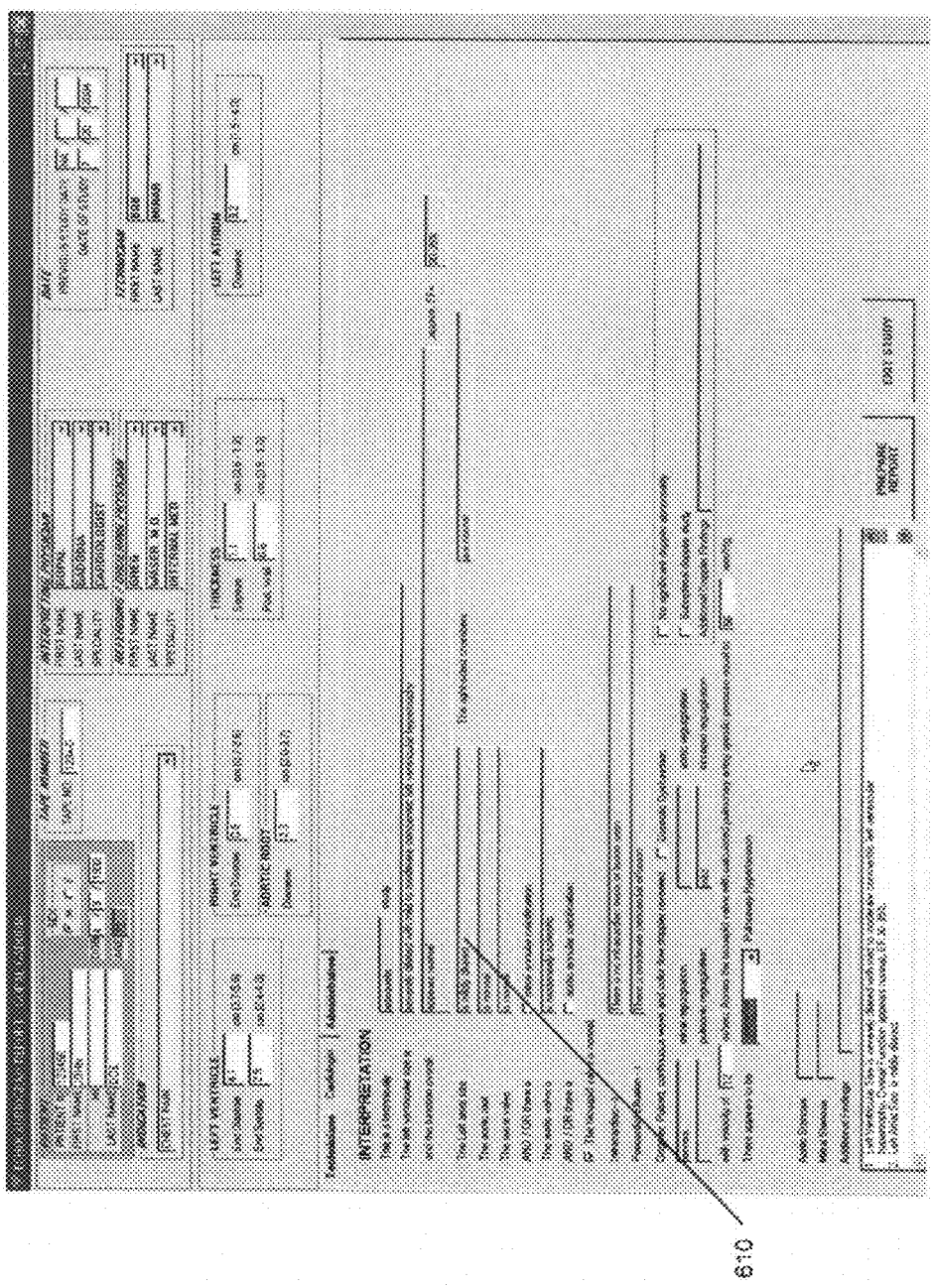
FIG. 6 illustrates a screen for display and physician's review of various evaluations by an interpretation engine according to an embodiment of the present invention.

FIG. 6 illustrates a screen for display and physician's review of various evaluations by the interpretation engine according to an embodiment of the present invention. As shown in FIG. 6, the main panel screen displays the machine evaluations by the interpretation engine 130 on the various interpretation fields 610. The physician can approve the evaluations made by the interpretation engine 130, make appropriate adjustments, or overrule the machine evaluations.

Figure 7:
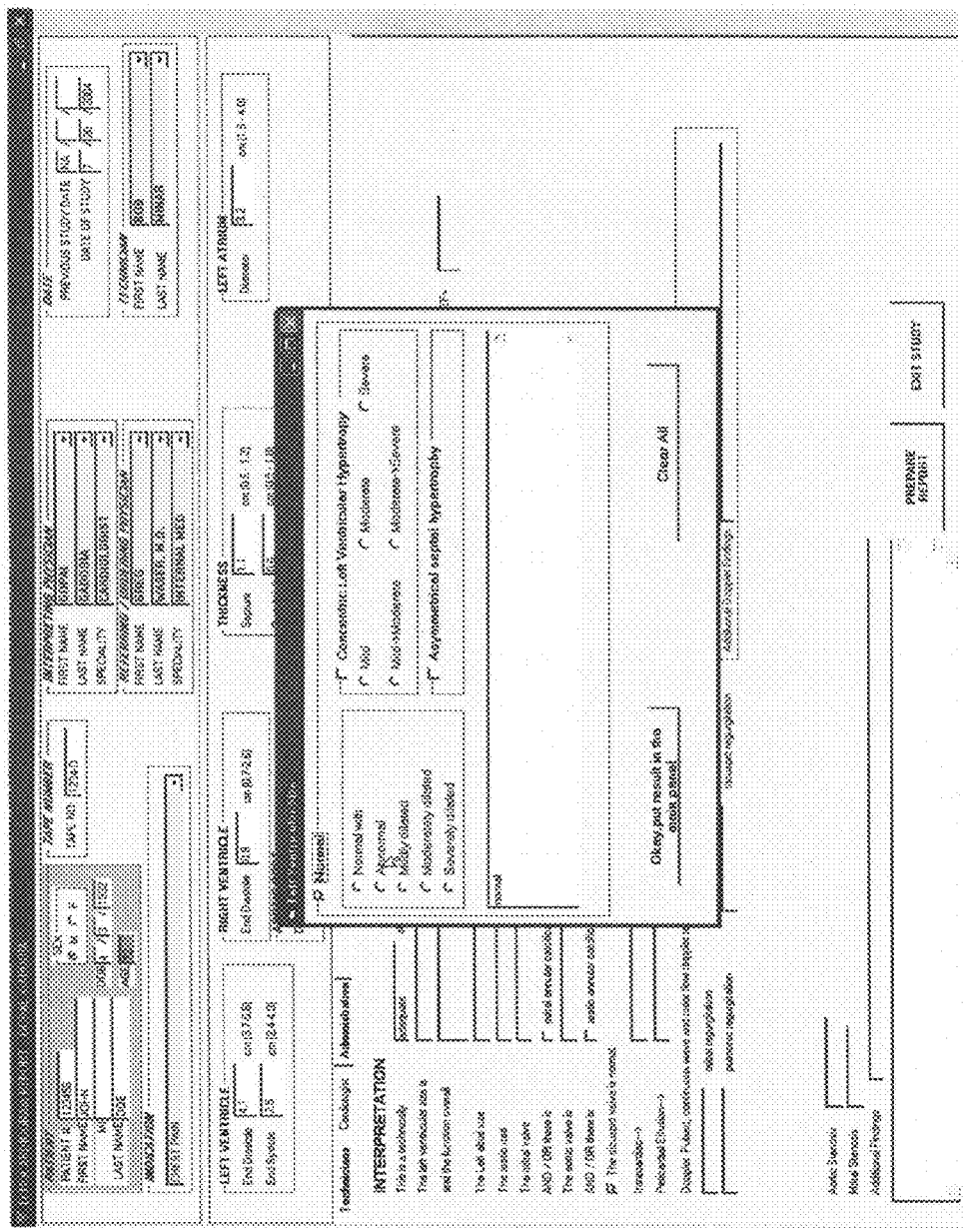
FIG. 7 illustrates a screen for a physician's reading and interpretation of left ventricle dilation and left ventricular hypertrophy according to an embodiment of the present invention.

FIG. 7 illustrates a screen for a physician's reading and interpretation of left ventricle dilation and left ventricular hypertrophy according to an embodiment of the present invention. When the user clicks the empty box in front of one of the lines of text, a dialogue box pops up. For example, when the user clicks the box in front of the left ventricular size (the second line under "Interpretation"), it shows whether it is normal, abnormal, or mildly dilated. If the user clicks on that, they will be prompted to enter whether it is hypertrophied or not.

Figure 8:
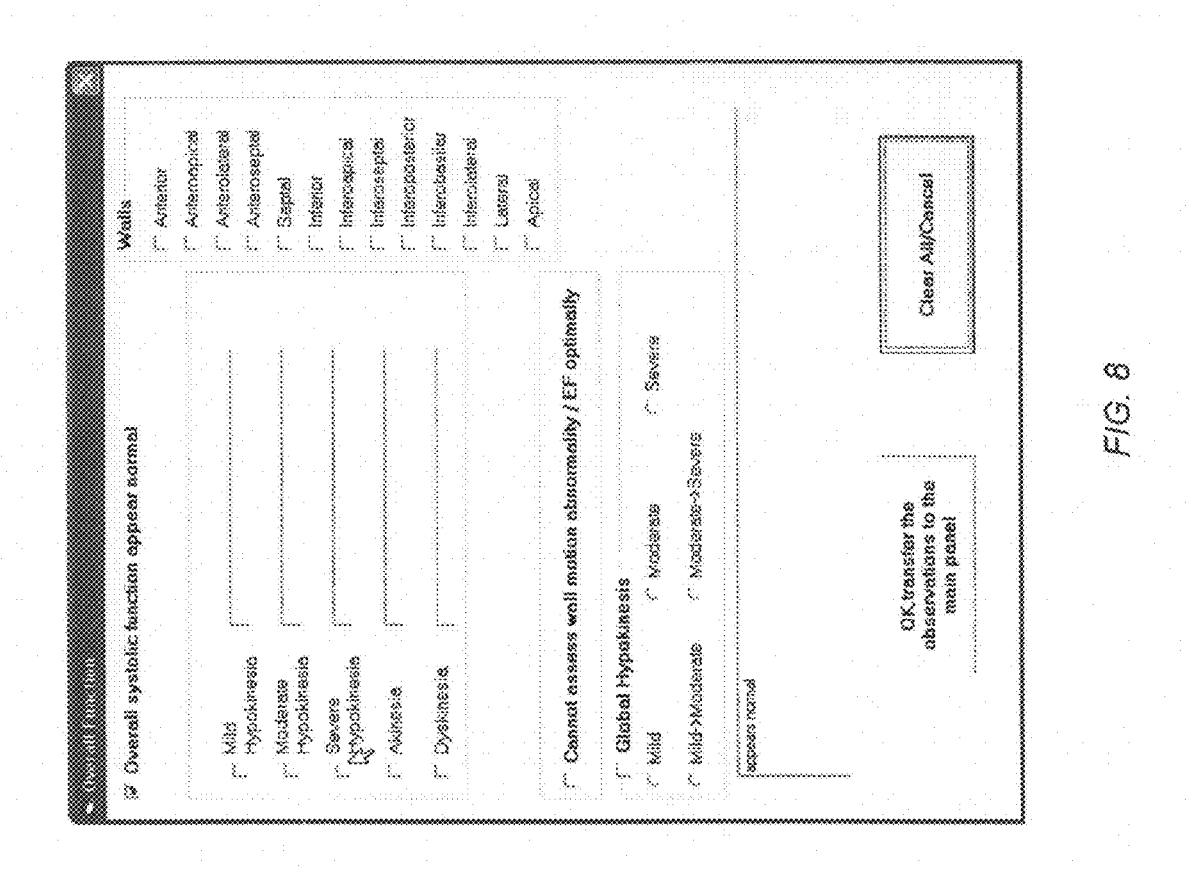

FIG. 8 likewise illustrates an exemplary screen for a physician's reading and interpretation of overall systolic function according to an embodiment of the present invention.

Figure 9:
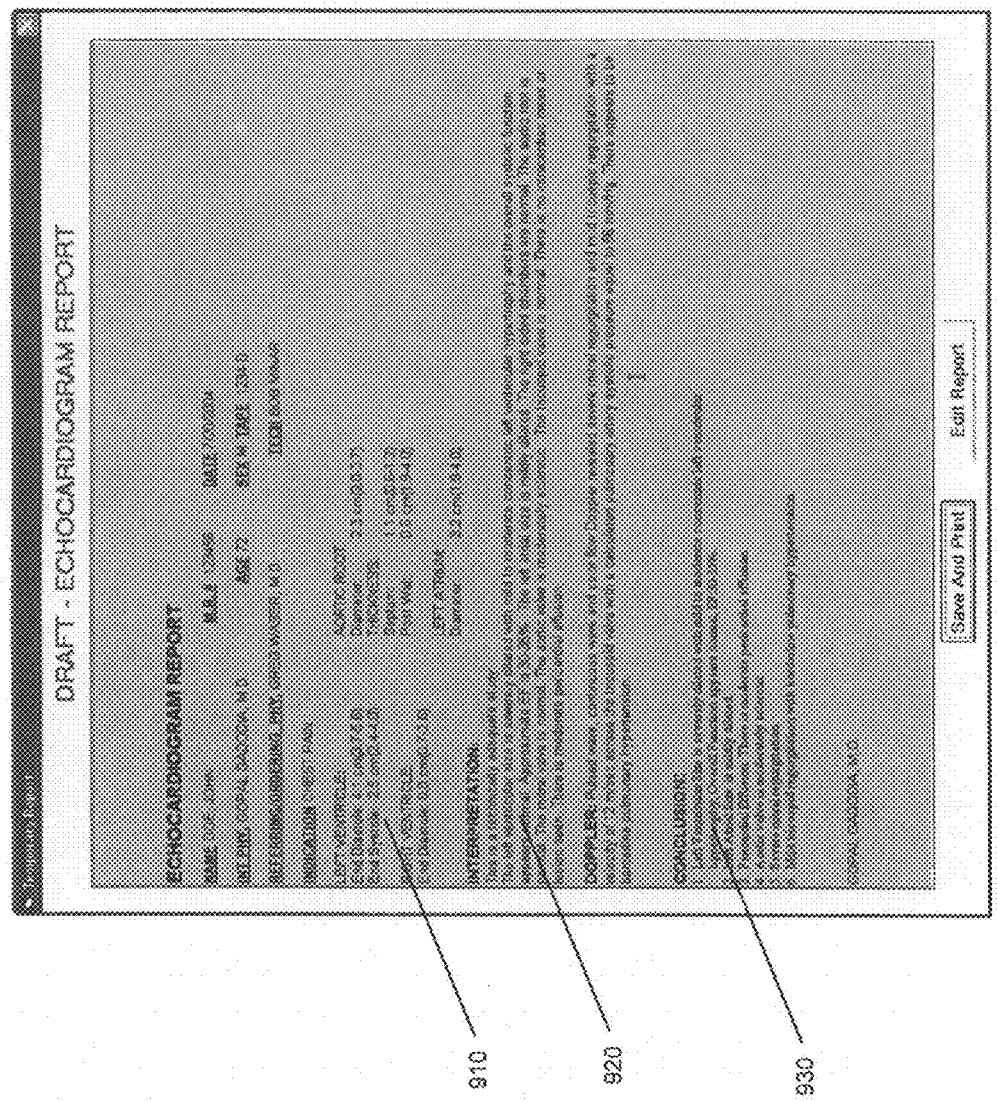
FIG. 9 illustrates a screen for displaying an echo cardiogram report according to an embodiment of the present invention.

Upon completion of the physician's review, the physician approved interpretations become diagnostic conclusions, and the report containing the results of the physician review is generated by the report generation engine 150. FIG. 9 illustrates a screen for displaying an echo cardiogram report according to an embodiment of the present invention. As shown in FIG. 9, the report according to the present invention contains all of the relevant information and data of the results of an echo cardiogram study, including, but not limited to, the measured dimensions 910, the interpretations 920, and the diagnostic conclusions 930.

The foregoing description of an exemplary embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A method for automated medical diagnostic interpretation and report generation for a non-invasive medical diagnostic test, the method comprising:
   receiving, by a computer, one or more structural dimension measurements and physiological measurements of the non-invasive medical diagnostic test from a non-invasive medical diagnostic device;
   interpreting, by using an artificial intelligence system or an expert system included in the computer, the received structural dimension measurements and physiological measurements;
   generating a diagnostic evaluation to be reviewed by a physician based on the interpretation; and
   generating a diagnostic report upon completion of the physician's review.

2. The method of claim 1, wherein the non-invasive medical diagnostic test is an echo cardiogram.

3. The method of claim 2, wherein the one or more structural dimension measurements and physiological measurements from the echo cardiogram test comprise:
   a measurement of the size of the left ventricle, the left atrium, the aortic root, and the right-sided chambers;
   a measurement of pericardial effusion; and
   a measurement of Doppler velocities across one or more heart valves, and
   wherein the diagnostic evaluation comprises:
   an evaluation of whether the left ventricle is normal in size or dilated;
   an evaluation of whether the left ventricle is hypertrophied;
   an evaluation of calcification;
   an evaluation of the existence of pathological mass or structure in the cardiac chamber cavity;
   an evaluation of a severity of pericardial effusion;
   an evaluation of a severity of regurgitation through a heart valve;
   an evaluation of tricuspid regurgitation;
   an evaluation of pulmonary hypertension; and
   an evaluation of aortic and mistral valve stenosis.

4. A method for automated medical diagnostic interpretation and report generation for an echo cardiogram test, the method comprising:
   receiving, by a computer, one or more structural dimension measurements and physiological measurements from an echo cardiogram test device, said one or more structural dimension measurements and physiological measurements including at least one of:
   a measurement of the size of the left ventricle, the left atrium, the aortic root, and the right-sided chambers;
   a measurement of pericardial effusion; and
   a measurement of Doppler velocities across one or more heart valves;
   interpreting, by using an artificial intelligence system or an expert system included in the computer, the received structural dimension measurements and physiological measurements;
   generating diagnostic evaluations to be reviewed by a physician based on the interpretation, the diagnostic evaluations including at least one of:
   an evaluation of whether the left ventricle is normal in size or dilated;
   an evaluation of whether the left ventricle is hypertrophied;
   an evaluation of calcification;
   an evaluation of the existence of pathological mass or structure in the cardiac chamber cavity;
   an evaluation of a severity of pericardial effusion;
   an evaluation of a severity of regurgitation through a heart valve;
   an evaluation of tricuspid regurgitation;
   an evaluation of pulmonary hypertension; and
   an evaluation of aortic and mistral valve stenosis; and
   generating a diagnostic report upon completion of the physician's review.

5. A system for automated medical diagnostic interpretation and report generation for a non-invasive medical diagnostic test, the system comprising:
   a computer;
   a medical diagnostic interpretation engine including an artificial intelligence or an expert system; and
   a report generation engine, wherein:
   the medical diagnostic interpretation engine running on the computer receives one or more structural dimension measurements and physiological measurements from a non-invasive medical diagnostic test device, interprets, by using the artificial intelligence or the expert system, the received structural dimension measurements and physiological measurements, and generates a diagnostic evaluation to be reviewed by a physician based on the interpretation, and
   upon completion of the physician's review, the report generation engine generates a diagnostic report.

6. The system of claim 5 wherein the non-invasive medical diagnostic test is an echo cardiogram test.

7. The system of claim 6, wherein the one or more structural dimension measurements and physiological measurements from the echo cardiogram test comprise:
   a measurement of the size of the left ventricle, the left atrium, the aortic root, and the right-sided chambers;
   a measurement of pericardial effusion; and
   a measurement of Doppler velocities across one or more heart valves, and
   wherein the diagnostic evaluation comprises:
   an evaluation of whether the left ventricle is normal in size or dilated;
   an evaluation of whether the left ventricle is hypertrophied;
   an evaluation of calcification;
   an evaluation of the existence of pathological mass or structure in the cardiac chamber cavity;
   an evaluation of a severity of pericardial effusion;
   an evaluation of a severity of regurgitation through a heart valve;

an evaluation of tricuspid regurgitation;
an evaluation of pulmonary hypertension; and
an evaluation of aortic and mistral valve stenosis.

8. A system for automated medical diagnostic interpretation and report generation for an echo cardiogram test, the system comprising:
a computer;
a medical diagnostic interpretation engine including an artificial intelligence or an expert system; and
a report generation engine, wherein:
the medical diagnostic interpretation engine running on the computer receives one or more structural dimensions and physiological measurements from an echo cardiogram test device, the one or more structural dimensions and physiological measurements including at least one of a measurement of the size of the left ventricle, the left atrium, the aortic root, and the right-sided chambers, a measurement of pericardial effusion, and a measurement of Doppler velocities across one or more heart valves;
the medical diagnostic interpretation engine interprets, by using the artificial intelligence or the expert system, the received structural dimensions and physiological measurements, and generates diagnostic evaluations to be reviewed by a physician based on the interpretation, the diagnostic evaluations including at least one of:
an evaluation of whether the left ventricle is normal in size or dilated;
an evaluation of whether the left ventricle is hypertrophied;
an evaluation of calcification;
an evaluation of the existence of pathological mass or structure in the cardiac chamber cavity;
an evaluation of a severity of pericardial effusion;
an evaluation of a severity of regurgitation through a heart valve;
an evaluation of tricuspid regurgitation;
an evaluation of pulmonary hypertension; and
an evaluation of aortic and mistral valve stenosis; and
upon completion of the physician's review, the report generation engine generates a diagnostic report.

9. The system of claim 8, further comprising:
an interface to the echo cardiogram test device for receiving said one or more structural dimension measurements and physiological measurements automatically from the echo cardiogram test device; and
a database for storing and retrieving patient records.

10. A system for automated medical diagnostic interpretation and report generation for an echo cardiogram test, the system comprising:
means for receiving one or more structural dimension measurements and physiological measurements from an echo cardiogram test device, the one or more structural dimension measurements and physiological measurements including at least one of:
a measurement of the size of the left ventricle, the left atrium, the aortic root, and the right-sided chambers;
a measurement of pericardial effusion; and
a measurement of Doppler velocities across one or more heart valves;
means for interpreting the received structural dimension measurements and physiological measurements, the means for interpreting including an artificial intelligence system or an expert system running on a computer;
means for generating diagnostic evaluations to be reviewed by a physician based on the interpretation, the diagnostic evaluation including at least one of:
an evaluation of whether the left ventricle is normal in size or dilated;
an evaluation of whether the left ventricle is hypertrophied;
an evaluation of calcification;
an evaluation of the existence of pathological mass or structure in the cardiac chamber cavity;
an evaluation of a severity of pericardial effusion;
an evaluation of a severity of regurgitation through a heart valve;
an evaluation of tricuspid regurgitation;
an evaluation of pulmonary hypertension; and
an evaluation of aortic and mistral valve stenosis; and
means for generating a diagnostic report upon completion of the physician's review.

11. Computer-executable process steps for automated medical diagnostic interpretation and report generation for an echo cardiogram test, the steps comprising:
a step for receiving, by a computer, one or more structural dimension measurements and physiological measurements from an echo cardiogram test device, the one or more structural dimension measurements and physiological measurements including all of:
a measurement of the size of the left ventricle, the left atrium, the aortic root, and the right-sided chambers;
a measurement of pericardial effusion; and
a measurement of Doppler velocities across one or more heart valves;
a step for interpreting, by using an artificial intelligence system or an expert system included in the computer, the received structural dimension measurements and physiological measurements;
a step for generating diagnostic evaluations to be reviewed by a physician based on the interpretation, the diagnostic evaluation including all of:
an evaluation of whether the left ventricle is normal in size or dilated;
an evaluation of whether the left ventricle is hypertrophied;
an evaluation of calcification;
an evaluation of the existence of pathological mass or structure in the cardiac chamber cavity;
an evaluation of a severity of pericardial effusion;
an evaluation of a severity of regurgitation through a heart valve;
an evaluation of tricuspid regurgitation;
an evaluation of pulmonary hypertension; and
an evaluation of aortic and mistral valve stenosis; and
a step for generating a diagnostic report upon completion of the physician's review.

12. The method of claim 1, further comprising receiving a modification of or an addition to the diagnostic evaluation by the physician, wherein
upon receiving an input representing an approval of the diagnostic evaluation from the physician, the diagnostic report reflecting the modification or the addition is generated and output.

13. The method of claim 1, wherein said one or more structural dimension measurements and physiological measurements includes a measurement of pericardial effusion, and the diagnostic evaluation includes an evaluation of a severity of pericardial effusion.

14. The method of claim 4, further comprising receiving a modification of or an addition to the diagnostic evaluation by the physician, wherein upon receiving an input representing an approval of the diagnostic evaluation from the physician, the diagnostic report reflecting the modification or the addition is generated and output.

15. The method of claim 4, wherein said one or more structural dimension measurements and physiological measurements includes a measurement of pericardial effusion, and the diagnostic evaluation includes an evaluation of a severity of pericardial effusion.

16. The system of claim 5, wherein:
the report generating engine receives a modification of or an addition to the diagnostic evaluation by the physician, and
upon receiving an input representing an approval of the diagnostic evaluation from the physician, the report generating engine generates and output the diagnostic report reflecting the modification or the addition.

17. The system of claim 5, wherein said one or more structural dimension measurements and physiological measurements includes a measurement of pericardial effusion, and the diagnostic evaluation includes an evaluation of a severity of pericardial effusion.

18. The system of claim 8, wherein:
the report generating engine receives a modification of or an addition to the diagnostic evaluation by the physician, and
upon receiving an input representing an approval of the diagnostic evaluation from the physician, the report generating engine generates and output the diagnostic report reflecting the modification or the addition.

19. The system of claim 8, wherein said one or more structural dimension measurements and physiological measurements includes a measurement of pericardial effusion, and the diagnostic evaluation includes an evaluation of a severity of pericardial effusion.

20. The system of claim 10, wherein:
the means for generating a diagnostic report receives a modification of or an addition to the diagnostic evaluation by the physician, and
upon receiving an input representing an approval of the diagnostic evaluation from the physician, the means for generating a diagnostic report generates and output the diagnostic report reflecting the modification or the addition.

21. The system of claim 10, wherein said one or more structural dimension measurements and physiological measurements includes a measurement of pericardial effusion, and the diagnostic evaluation includes an evaluation of a severity of pericardial effusion.

* * * * *